US 9,295,582 B2

(12) United States Patent
Rockley et al.

(10) Patent No.: US 9,295,582 B2
(45) Date of Patent: Mar. 29, 2016

(54) FLUIDICS ADJUSTMENT TECHNIQUES FOR USE IN A SURGICAL PROCEDURE

(71) Applicant: Abbott Medical Optics Inc., Santa Ana, CA (US)

(72) Inventors: Paul W. Rockley, Corona Del Mar, CA (US); Erik C. Kramme, Chicago, IL (US); Thomas Buico, Northglenn, CO (US)

(73) Assignee: Abbott Medical Optics Inc.

( * ) Notice: Subject to any disclaimer, the term of this patent is extended or adjusted under 35 U.S.C. 154(b) by 292 days.

(21) Appl. No.: 13/799,137

(22) Filed: Mar. 13, 2013

(65) Prior Publication Data

US 2014/0276897 A1    Sep. 18, 2014

(51) Int. Cl.
| | |
|---|---|
| *G08B 21/00* | (2006.01) |
| *G08B 13/20* | (2006.01) |
| *A61F 9/00* | (2006.01) |
| *G06F 3/048* | (2013.01) |
| *A61B 17/20* | (2006.01) |
| *A61F 9/007* | (2006.01) |
| *G06F 3/0484* | (2013.01) |

(52) U.S. Cl.
CPC .......... *A61F 9/00745* (2013.01); *A61F 9/00736* (2013.01); *G06F 3/0484* (2013.01)

(58) Field of Classification Search
CPC .................................................. A61F 9/00745
USPC ........................................................ 340/540
See application file for complete search history.

(56) References Cited

U.S. PATENT DOCUMENTS

| | | | | |
|---|---|---|---|---|
| 3,369,812 | A | * | 2/1968 | McKee .......................... 473/192 |
| 4,670,006 | A | * | 6/1987 | Sinnett et al. .................... 604/26 |
| 5,674,130 | A | * | 10/1997 | Egan .............................. 473/132 |
| 6,251,113 | B1 | | 6/2001 | Appelbaum et al. |
| 6,974,391 | B2 | * | 12/2005 | Ainsworth et al. ........... 473/153 |

(Continued)

FOREIGN PATENT DOCUMENTS

| | | |
|---|---|---|
| EP | 1905401 A2 | 4/2008 |
| WO | WO-9613216 A1 | 5/1996 |

OTHER PUBLICATIONS

Fluidics in Modern Vitrectomy—Highlights from an Expert Roundtable Meeting, A Supplement to Ophthalmology Times, Apr. 2010, 15 pages.

(Continued)

*Primary Examiner* — Jennifer Mehmood
*Assistant Examiner* — John Mortell
(74) *Attorney, Agent, or Firm* — Abbott Medical Optics Inc.

(57) ABSTRACT

An apparatus and method for controlling fluid flow to an ocular region is provided. The apparatus includes a control unit having a processor, a user interface configured to receive data from the processor and provide information to an operator, and a memory unit configured to provide information to the processor. The memory unit includes a lookup table configured with a plurality of fluid parameter related conditions potentially expected to be encountered during a phacoemulsification procedure and a plurality of warning entries, each warning entry associated with fluid parameter related conditions potentially expected to be encountered during the phacoemulsification procedure. Each warning entry corresponding to a level of performance outside a predetermined range is conveyed to the operator via the user interface and in certain instances functionality of the apparatus may be altered.

35 Claims, 10 Drawing Sheets

(56) References Cited

U.S. PATENT DOCUMENTS

| | | | | |
|---|---|---|---|---|
| 6,998,965 B1* | 2/2006 | Luciano et al. | | 340/323 R |
| 2004/0068199 A1* | 4/2004 | Echauz et al. | | 600/544 |
| 2005/0051951 A1* | 3/2005 | Benevento | | 273/120 R |
| 2005/0272496 A1* | 12/2005 | Reinish et al. | | 463/2 |
| 2008/0006096 A1* | 1/2008 | Gordon et al. | | 73/861.43 |
| 2008/0021651 A1* | 1/2008 | Seeley et al. | | 702/3 |
| 2010/0304876 A1* | 12/2010 | Hohla et al. | | 473/199 |
| 2011/0166505 A1* | 7/2011 | Kadziauskas et al. | | 604/22 |

OTHER PUBLICATIONS

International Search Report and Written Opinion for Application No. PCT/US2014/018574, mailed on Jul. 21, 2014, 15 pages.

* cited by examiner

FLUIDICS ADJUSTMENT TECHNIQUES FOR USE IN A SURGICAL PROCEDURE

BACKGROUND

1. Field

The present invention relates generally to fluid management during a surgical procedure, and more specifically to monitoring fluidics parameters and acting to prevent potential harm during a surgical procedure, such as an ocular surgical procedure.

2. Background

Surgical systems, such as phacoemulsification systems for ophthalmic surgery, require an infusion of fluid into a patient's eye while the surgery is being performed. Accurate management of such fluid infusion is critical to the procedure. In the phacoemulsification surgical context, the surgeon employs a phacoemulsification machine that controls fluid flow to the ocular region of the patient. If fluid flow is inadequate during the ocular surgical procedure, an adverse and potentially catastrophic situation can develop, possibly causing severe damage to the patient.

Fluid flow is typically controlled during an ophthalmic or ocular surgical procedure in part by the phacoemulsification machine adjusting the height of an infusion bottle or other irrigation fluid source. Other parameters or attributes of the fluid path can materially affect fluid flow to the eye, including but not limited to incision size and the dimensions of the fluid delivery device, such as outer diameter of the needle being employed in an ocular surgical handpiece, inner diameter of the needle and size(s) of other fluid passages in the fluid path, and incision leakage effects. As an example, different sleeves provided on different phacoemulsification handpieces can have varying fluid path diameters and consequently can deliver different amounts of fluid.

Newer phacoemulsification devices also employ different types of pumps, including volumetric pumps (e.g. peristaltic pumps) and vacuum pumps (e.g. Venturi pumps). Certain surgeons prefer to use one type of pump over another in certain surgical situations, while others prefer to operate by occasionally switching between pumps. Pump settings and accessories, such as phaco needle tip size and lumen size, can be matched to the expected fluid characteristics of the system. For example, if a surgeon is expecting to use only peristaltic pumping to infuse the eye, she may employ a certain sleeve having a particular gauge (fluid opening size). If switching between pumps is desired, such functionality can be provided to the surgeon, enabling him to manually or automatically switch between pumps at certain times or under certain conditions, depending on the risks involved.

Other issues may arise, such as in the situation where the surgeon employs an incision knife during the surgical procedure. Problems may arise when the opening made by such an incision knife is large relative to the inner and outer diameters of the sleeve employed on the handpiece and the outer diameter of the tip employed. Additionally, fluid flow is typically varied in these procedures by varying height of a BSS bottle, and changes in bottle height can affect the flow into and through a sleeve and tip when employed in the presence of different types of pumps.

Certain combinations of the foregoing fluid devices, parameters, and settings employed can result in unforeseen conditions. As an example, when switching between peristaltic and Venturi pumps, employing a certain phaco tip and sleeve in the presence of a particular incision size and using a certain bottle height, inadequate fluid may be provided to the ocular region. Such an arrangement can, in absolute worst case scenarios, result in anterior ocular chamber collapse or iris prolapse when switching between pump functions.

The difficulty for the surgeon is knowing when these potentially hazardous conditions may occur. Surgeons and other operating room personnel are typically focused on various other tasks, and personnel present may simply not know when a dangerous situation may occur, or when a potentially harmful set of conditions is present.

There is therefore a need in the art for techniques and devices that can provide efficient and effective notice to the surgeon that a potentially dangerous condition may occur with respect to fluid flow to the eye of the patient. In certain instances, there may be a need to alter functionality in the case of a potentially dangerous situation. It would therefore be beneficial to provide a design that overcomes fluid management issues present in systems known in the art.

SUMMARY

Thus according to one aspect of the present invention, there is provided a phacoemulsification device configured to receive fluid from a fluid maintaining device, the phacoemulsification device fluidly attached to a handpiece. The phacoemulsification device includes a control unit comprising a processor, a user interface configured to receive data from the processor and provide information to an operator, and a memory unit configured to provide information to the processor. The memory unit comprises a lookup table configured with a plurality of fluid parameter related conditions potentially expected to be encountered during a phacoemulsification procedure and a plurality of warning entries. Each warning entry is associated with fluid parameter related conditions potentially expected to be encountered during the phacoemulsification procedure. Each warning entry having severity above a predetermined level is conveyed to the operator via the user interface. In certain instances, each warning entry corresponding to a level of performance outside a predetermined range is not conveyed to the operator. In certain instances, functionality of the apparatus may be altered.

Alternately, the present design may include a method of preparing for conducting a phacoemulsification procedure. The method may include querying a lookup table maintained on a control unit of a phacoemulsification device, the lookup table comprising a plurality of fluid parameter related conditions potentially expected to be encountered during the phacoemulsification procedure and a plurality of warning entries, each warning entry associated with fluid parameter related conditions potentially expected to be encountered during the phacoemulsification procedure, and issuing a warning to an operator when a warning entry for one fluid parameter related conditions potentially expected to be encountered during the phacoemulsification procedure correspond to a level of performance outside a predetermined range.

In certain situations, when risks are considered acceptable, the present design may alter performance, such as switching aspiration and/or vacuum settings as pumps are switched, such as from peristaltic to Venturi. Such a system employs sensors and information obtained together with a lookup table and alters device performance based on conditions encountered and desired performance for the conditions encountered.

Other features and advantages of the present invention should be apparent from the following description of exemplary embodiments, which illustrate, by way of example, aspects of the invention.

DETAILED DESCRIPTION

One aspect of the present invention is the ability for a surgeon performing an ocular surgical procedure to receive a warning that conditions relating to fluid pressure may or will cause an adverse condition in the patient. The present design employs a specialized lookup table (LUT) taking several conditions and parameters into account, and provides the surgeon or other operating room personnel either with a warning, such as before beginning the surgical procedure by displaying a warning on a graphical user interface provided with the device used to perform the procedure. Alternately, if the risks are acceptable, the present design may employ the LUT to override certain requests or commands during the surgical procedure to avoid damaging or potentially catastrophic conditions, in most cases with appropriate warnings or cautions before or during the override procedure.

The present description is divided into four general sections. The first section describes the general operation of a phacoemulsification machine. The second section describes dual pump operation, particularly with reference to the dual pump cassette that may be employed in the phacoemulsification machine described herein. The third section describes fluid flow with respect to a handpiece that may be employed with the present design, and the fourth section explains operation of the warning system employed with the other components and devices discussed.

System Example

Figure 1:
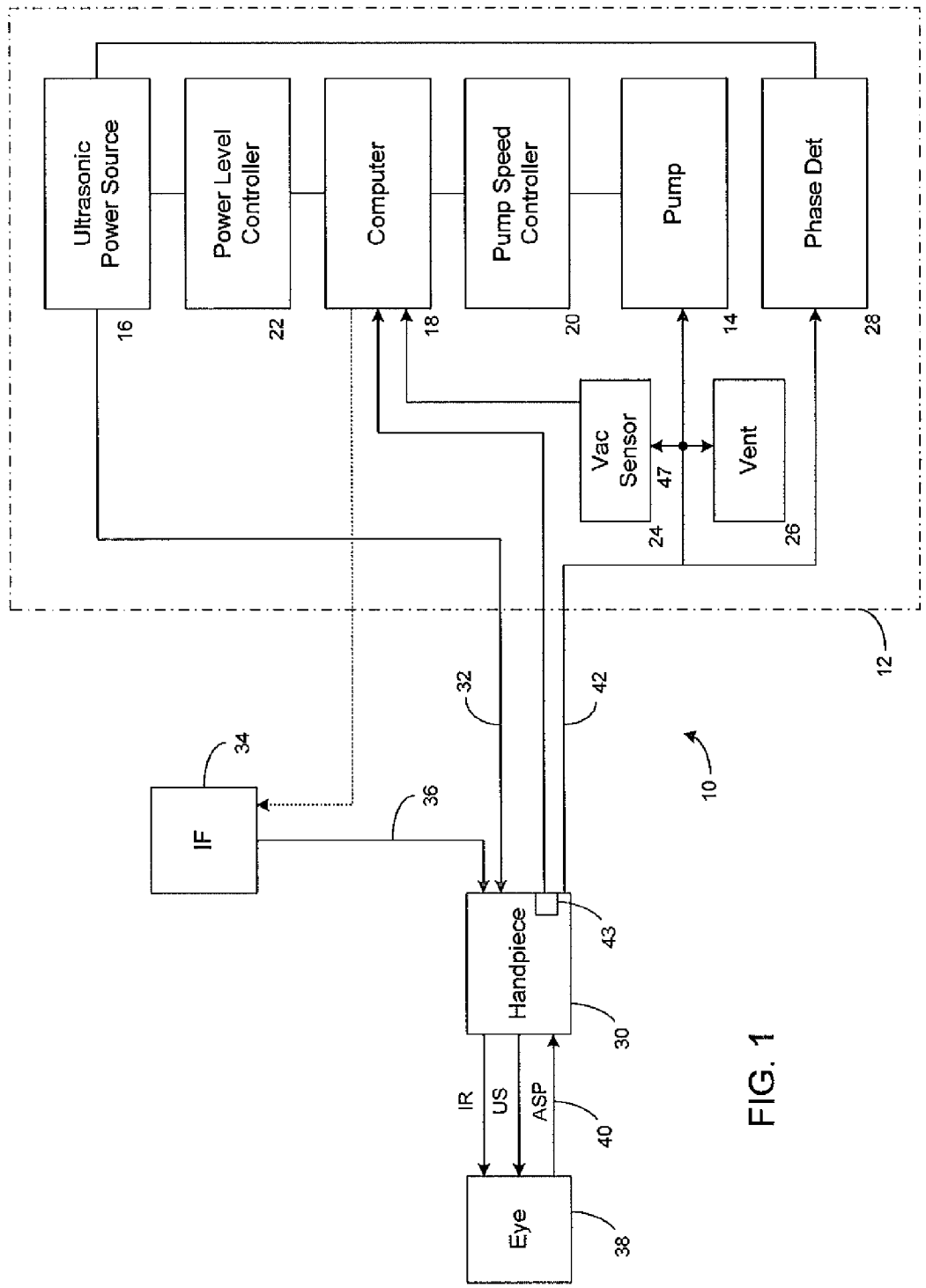
FIG. 1 illustrates a typical phacoemulsification system.

FIG. 1 illustrates a typical phacoemulsification system 10. The system includes a control unit 12, indicated by the dashed lines in FIG. 1 which includes a pump 14, a source of pulsed ultrasonic power 16, and a microprocessor computer 18 that provides control outputs to pump speed controller 20 and ultrasonic power level controller 22. Vacuum sensor 24 provides an input to computer 18 representing the vacuum level on the input side of pump 14. Suitable venting is provided by vent 26. Examples of pump 14 include a volumetric (e.g. peristaltic) pump and a vacuum (e.g. Venturi) pump, but other types of pumps may be employed.

While a single pump 14 is shown in FIG. 1, it is to be understood that more than one pump may be provided as discussed in further detail below.

Phase detector 28 provides an input to computer 18 representing a phase shift between a sine wave representation of the voltage applied to handpiece/needle 30 and the resultant current into handpiece 30. The block representation of handpiece 30 includes a needle and electrical means, typically a piezoelectric crystal, for ultrasonically vibrating the needle. Control unit 12 supplies power on line 32 to phacoemulsification handpiece/needle 30. An irrigation fluid source 34 is fluidly coupled to handpiece/needle 30 through line 36. The irrigation fluid and ultrasonic power are applied by handpiece/needle 30 to a patient's eye, or affected area or region, indicated diagrammatically by block 38, and may include a lumen (not shown). Alternatively, the irrigation source may be routed to eye 38 through a separate pathway independent of the handpiece. Eye 38 is aspirated by the pump 14 through line/handpiece needle 40 and line 42. Again, pump 14 may be a Venturi pump or a volumetric pump, such as a peristaltic pump, or a combination of both. Switch 43 disposed on handpiece 30 may be utilized as a means for enabling a surgeon/operator to select an amplitude of electrical pulses to the handpiece via computer 18, power level controller 22 and ultrasonic power source 16 as discussed herein. Any suitable input means, such as, for example, a foot pedal (not shown) may be utilized in lieu of switch 43.

FIG. 1 illustrates a dotted line connecting computer 18 with irrigation fluid source 34. In this arrangement, the computer may determine that in certain circumstances irrigation flow functionality is to be controlled as described in more detail below.

Figure 2:
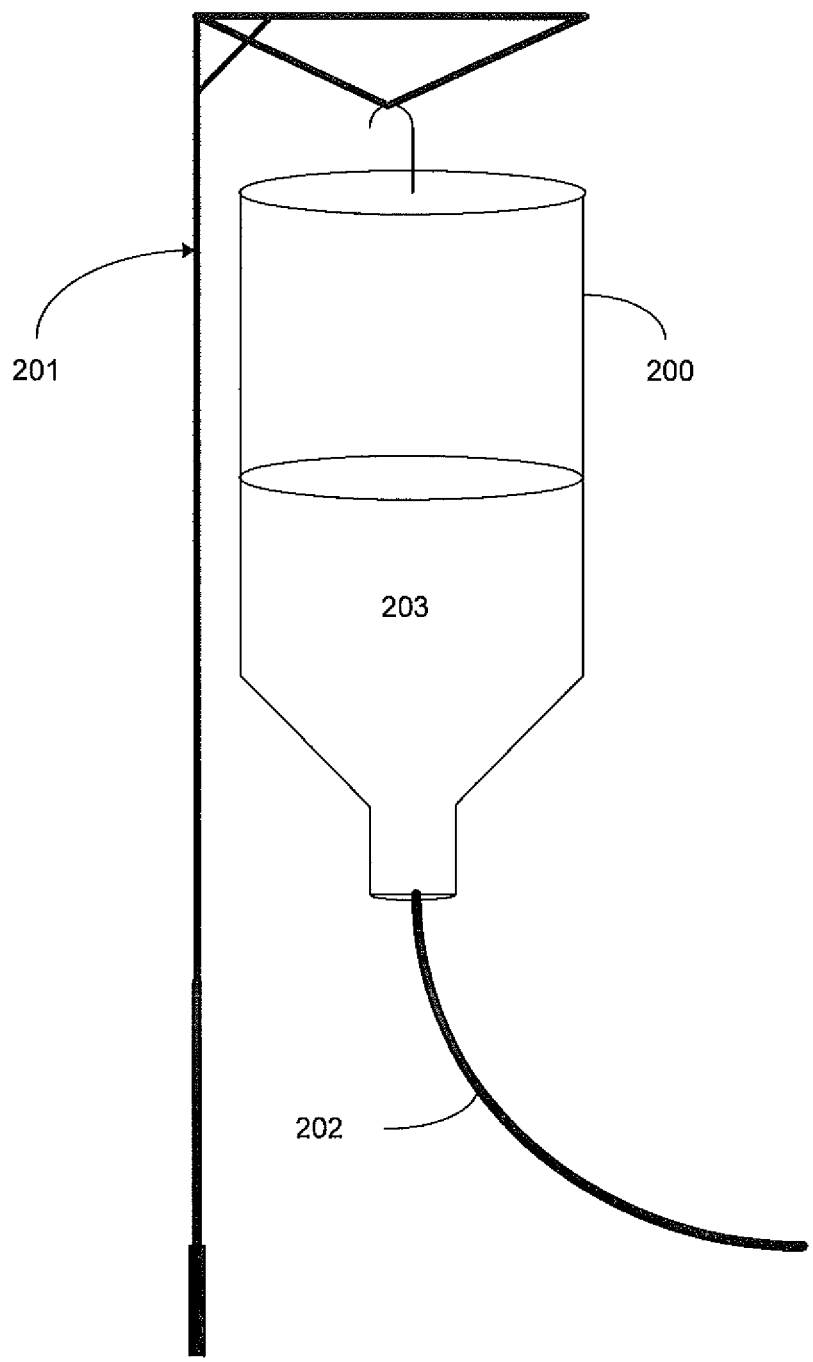
FIG. 2 is one example of an irrigation fluid source in the form of a BSS (balanced salt solution) bottle.

Irrigation fluid source 34 typically takes the form of infusion bottle 200 containing fluid 203, an example of which is shown in FIG. 2. Other irrigation fluid sources may be employed, such as a collapsible bag or other fluid maintaining device. The irrigation fluid source is typically placed on a device such as the retractable metal tube or tube arrangement 201 shown in FIG. 2 and controllable by control unit 12. In essence, control unit 12 commands the retractable metal tube or tube arrangement to extend or retract, thereby raising or lowering irrigation fluid source 34 and altering fluid flow through a line or tube such as line 202 in FIG. 2. The result of raising and lowering a bottle 200 is an increased or decreased rate of fluid flow. Fluid may also be provided from a reservoir subjected to variable pressurization, where pressurization of the reservoir results in delivery of fluid to a surgical handpiece and the ocular region.

Dual Pump Operation

The phacoemulsification system 10 of FIG. 1 may employ multiple pumps, e.g. a volumetric (peristaltic) and a vacuum (Venturi) pump, together in a dual pump cassette. Any types or combinations of pumps available may be employed, but for the present design a volumetric (peristaltic) and vacuum (Venturi pump is discussed, but the invention is not so limited. The design may employ a multiple pump cassette employed to coordinate fluid flow from multiple pumps. One example of a dual pump cassette design usable in the present design is provided in FIGS. 3A and 3B. The size and shape of cassette 350 is not to scale nor accurately sized, and note that certain components, notably peristaltic pump 303, interface with the cassette but in actuality form part of the device which the cassette attaches to. Further, more or fewer components may be included in the cassette than are shown in FIGS. 3A and 3B depending on the circumstances and implementation of the cassette arrangement 350.

Figure 3A:
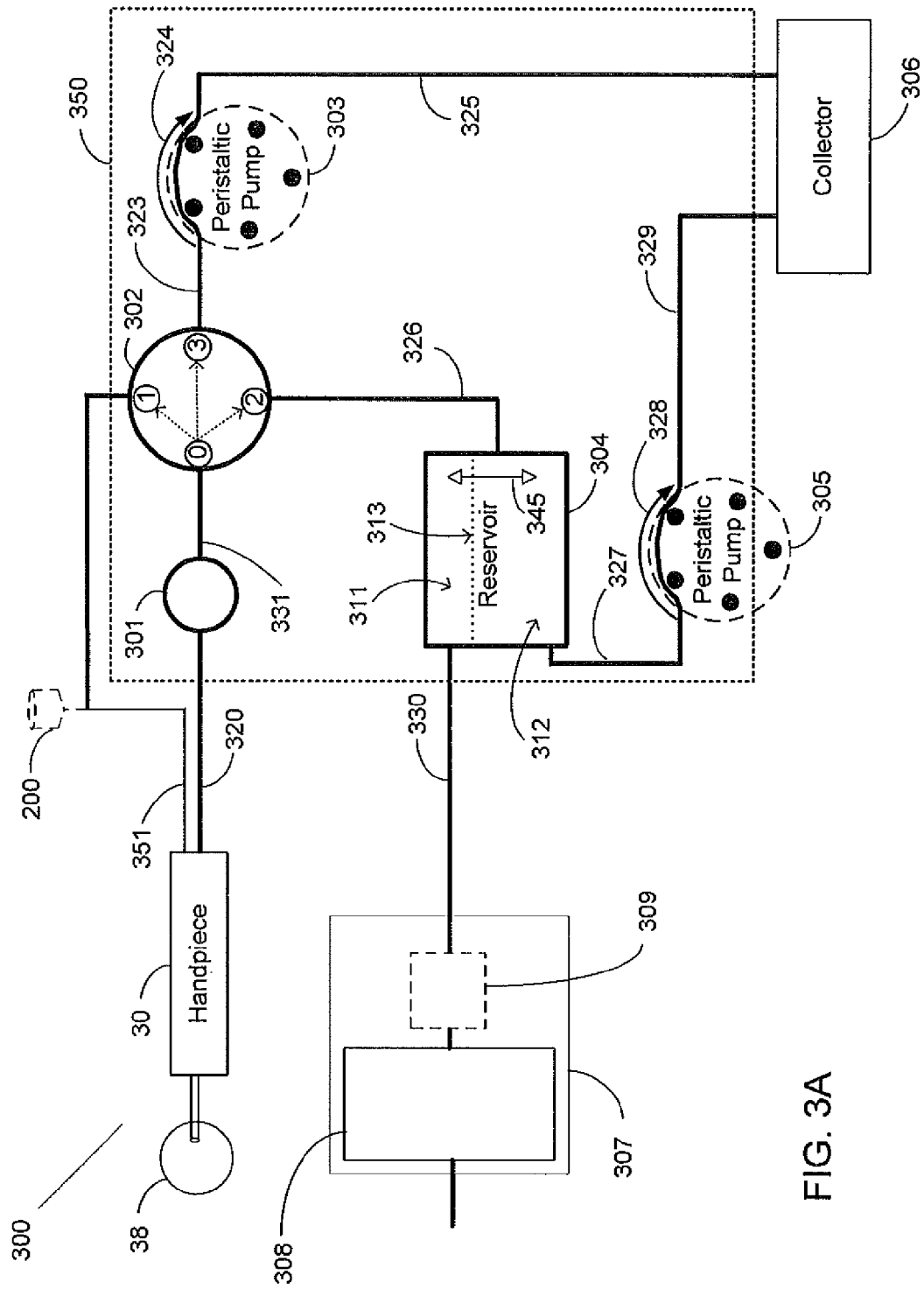
FIG. 3A shows a conceptual view of a device configured to employ both volumetric (peristaltic) and vacuum (Venturi) pump functionality.

Referring to FIG. 3A, handpiece 30 is connected to the input side of fluid vacuum sensor 301, typically by fluid pathways such as fluid pathway 320. The output side of fluid vacuum sensor 301 is connected to flow selector valve 302 within cassette arrangement 350 via fluid pathway 321. Flow selector valve 302 may interface between handpiece 30, irrigation fluid source 34 shown as BSS bottle 200, pump 303, which is shown as a peristaltic pump but may be another type of pump, and reservoir 304. In this configuration, the system may operate flow selector valve 302 to connect handpiece 30 with BSS bottle 200, reservoir 304 via line 351, or with pump 303 based on signals received from the surgeon via, for example, a graphical user interface provided with the control unit 12.

Figure 3B:
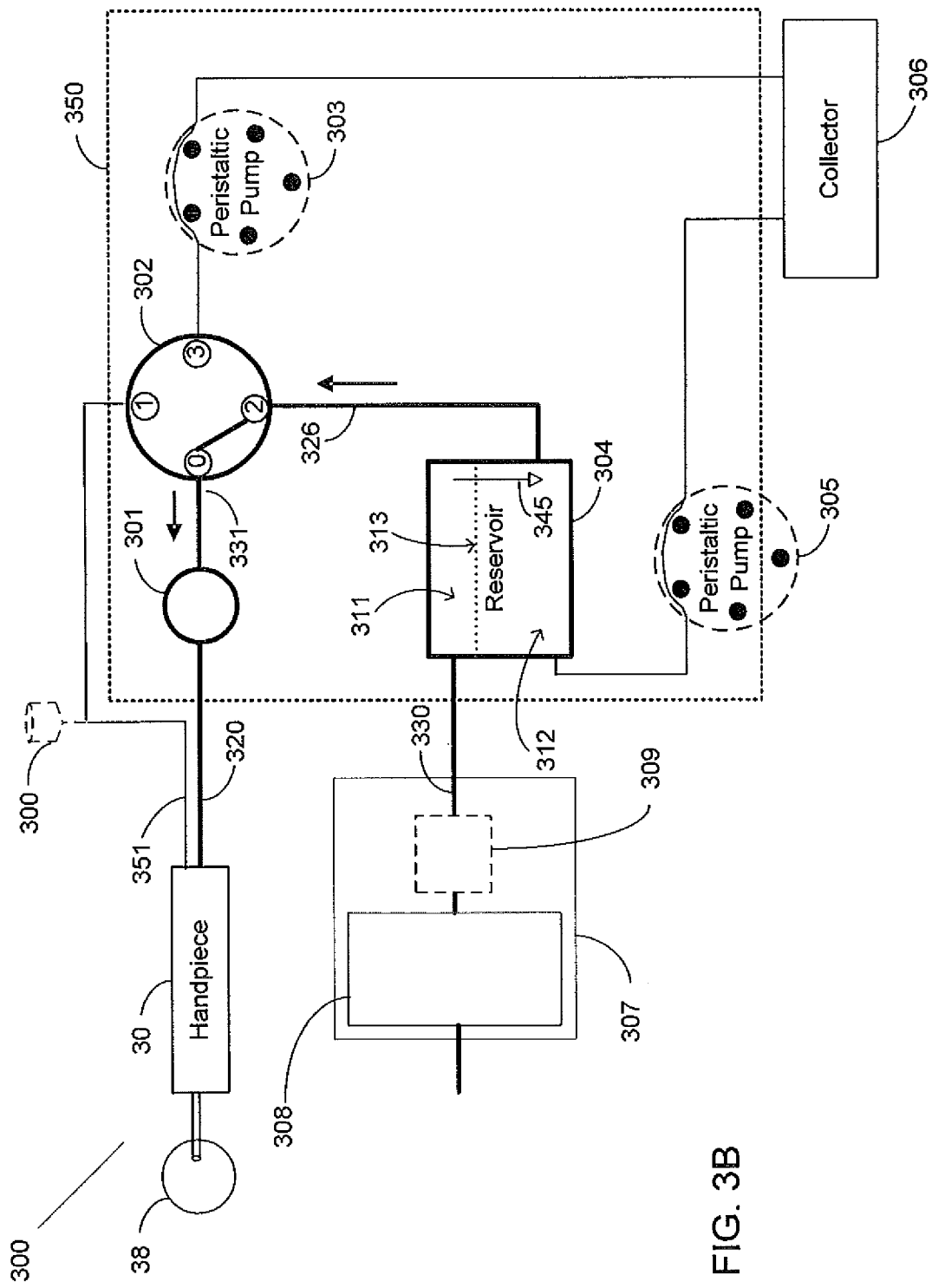
FIG. 3B shows an alternate conceptual view of a device configured to employ two types of pumps.

The flow selector valve 302 illustrated in FIGS. 3A and 3B provides a single input port and may connect port '0' to one of three available ports numbered '1', '2', and '3'.

Reservoir 304 may contain air in section 311 and fluid in section 312. Fluid may move up or down as indicated by arrow 345. Surgical cassette system 300 may connect reservoir 304 with collector 306 using fluid pathways, such as surgical tubing or similar items. In this arrangement, pump 305 may operate in a clockwise direction in the direction of arrow 328 to remove fluid from the reservoir 304 through fluid pathway 327 and deliver the fluid to collector 306 using fluid pathway 329. The peristaltic pump is illustrated as pump 305, and is a component within phacoemulsification system 10, but other types of pumps may be employed. This configuration may enable the surgical cassette 300 to remove unwanted fluid and/or material from reservoir 304. Fluid may alternately pass through fluid pathway 323 to pump 303, fluid pathway 325, and into collector 306 in certain situations.

The fluid pathways or flow segments of surgical cassette system 300 may include the fluid connections, for example flexible tubing, between each component represented with solid lines in FIGS. 3A and 3B.

Vacuum pump arrangement 307 is typically a component within phacoemulsification system 10, and may be connected with reservoir 304 via fluid pathway or flow segment 330. In the configuration shown, vacuum pump arrangement 307 includes a pump 308, such as a Venturi pump, and an optional pressure regulator 309 (and valve (not shown)), but other configurations are possible. In this arrangement, vacuum pump arrangement 307 may operate to remove air from the top of reservoir 304 and deliver the air to atmosphere (not shown). Removal of air from reservoir 304 in this manner may reduce the pressure within the reservoir, which reduces the pressure in the attached fluid pathway 326, to a level less than the pressure within eye 38. A lower reservoir pressure connected through flow selector valve 302 may cause fluid to move from the eye 38, thereby providing aspiration. The vacuum pump arrangement 307 and reservoir 304 can be used to control fluid flow into and out of reservoir 304.

The optional pressure regulator 309 may operate to add air to the top of reservoir 304 which in turn increases pressure and may force the air-fluid boundary 313 to move downward. Adding air into reservoir 304 in this manner may increase the air pressure within the reservoir, which increases the pressure in the attached fluid aspiration line 326 to a level greater than the pressure within eye 38. A higher reservoir pressure connected through flow selector valve 303 may cause fluid to move toward eye 38, thereby providing venting or reflux.

FIG. 3B illustrates an optional embodiment illustrating a surgical cassette system 300 configured for venting and/or reflux operation. The FIG. 3B design has flow selector valve 302 configured to connect handpiece 30 with reservoir 304 from port '2' to port '0'. Vacuum pump arrangement 307 may operate to provide pressure to reservoir 304 via pressure regulator 309. Applying or increasing pressure using pressure regular 309 of vacuum pump arrangement 307 may move air-fluid boundary 313 downward in the direction of arrow 345 causing fluid to flow from reservoir 304 and/or fluid pathway 326 to eye 38.

Figure 3C:
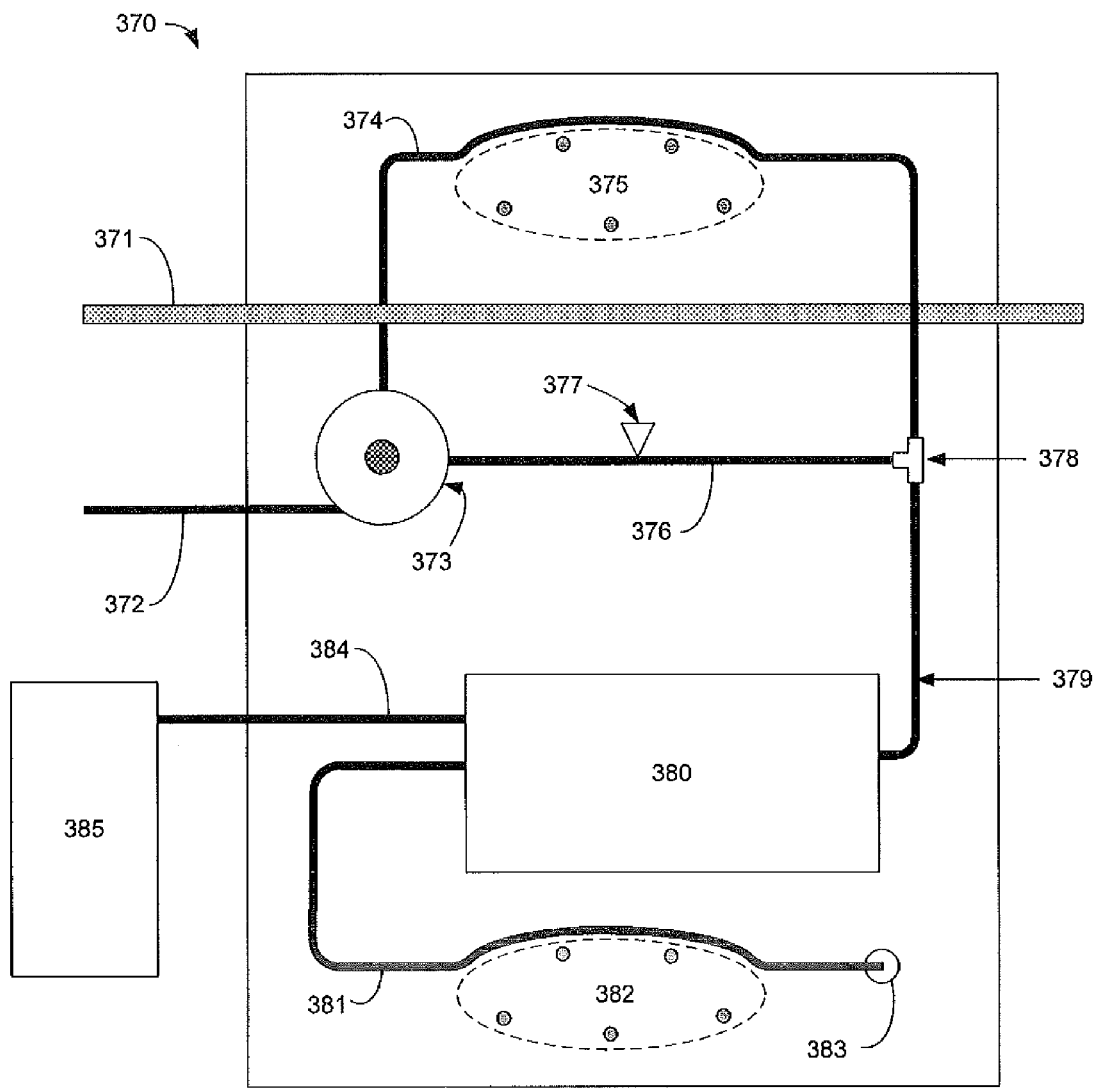
FIG. 3C illustrates an alternate dual pump cassette construction.

FIG. 3C illustrates an alternate dual pump cassette design 370. From FIG. 3C, irrigation line 371 receives fluid from a fluid source, not shown in this view but conceptually located on the right side of the cassette 370, and provides fluid to a handpiece, also not shown but conceptually positioned on the left side of the cassette. Fluid from the same handpiece or a different handpiece is received via aspiration line 372 and passes to pressure transducer 373. Pressure transducer 373 may include or unction as a vacuum sensor, causing fluid to selectively pass to one of two lines, upper line 374 and lower line 376. Upper line 374 interfaces with upper peristaltic pump 375, illustrated but not part of cassette 370, to provide fluid through joint 378 and line 379 to reservoir 380. Lower line 376 is controlled using valve 377 but also provides fluid to through joint 378 and line 379 to reservoir 380. Lower peristaltic pump 382, again illustrated but not part of cassette 370, draws fluid from reservoir 380 and moves fluid through drainage line 381 and out of port 383 leading to a collection bag (not shown). A vacuum pump arrangement 385 is provided (in the system console) and interfaces with reservoir 380 shown as line 384 such that pressure is applied to reservoir 380. Application of vacuum pressure in this manner causes fluid to be drawn to reservoir 380 from the handpiece through pressure transducer 373, line 376, joint 378, and line 379. The vacuum pump arrangement 385 and reservoir 380 act as a Venturi pump to draw fluid and debris from the eye via the handpiece.

Handpiece

Figure 4A:
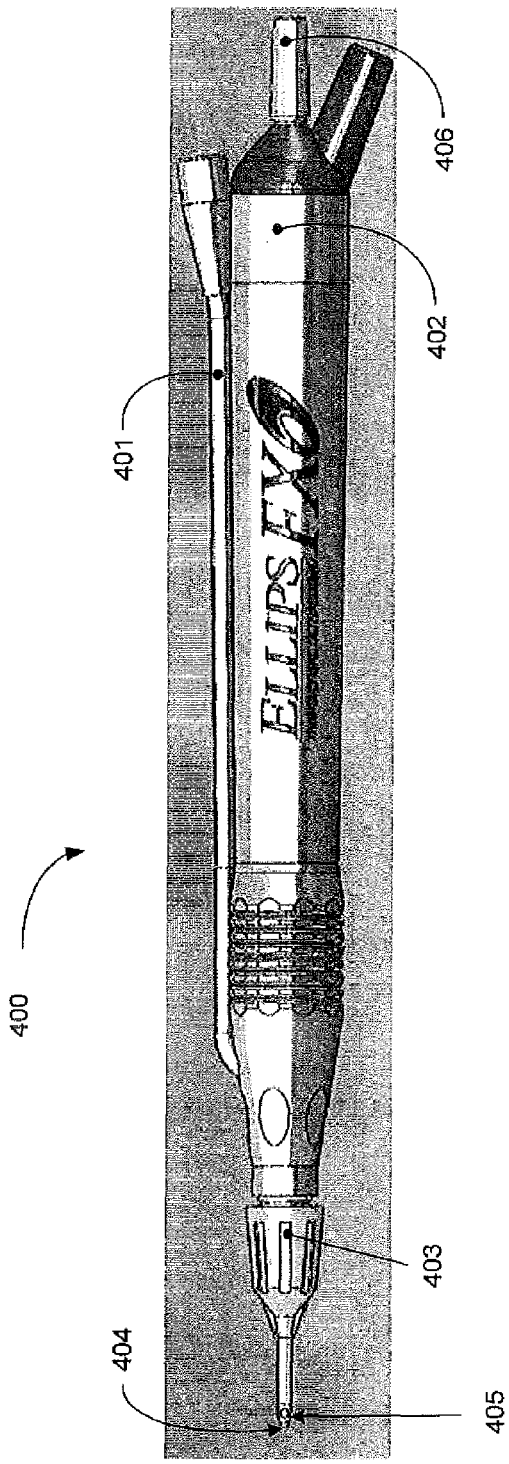
FIG. 4A is a representative handpiece that may be employed in the present design.

FIG. 4A illustrates a representative handpiece 400 employable with the present design. From FIG. 4A, handpiece 400 includes fluid line 401, base 402, and sleeve 403 is shown. Sleeve 403 houses phacoemulsification needle 404, operated using ultrasonic energy, and shown through the port 405 near the tip of sleeve 403. Different sleeves may employ different fluid openings, and in certain instances, a visual indication may be provided to indicate the fluid opening of the sleeve. As an example, different colors may be used to indicate different fluid opening sizes, e.g. a blue sleeve has an opening of X gauge. Different needles may also be employed having different sized inner/outer diameters, shapes, e.g. 19, 20, 21 gauge needle tips; or straight, bent, or flared needles; different bevels or no bevel as the distal end of the needle. Aspiration line 406 is used to remove fluid from the surgical site, e.g. the eye.

The handpiece 400 of FIG. 4A receives fluid from the phacoemulsification system 10 using cassette 350, 370 and tubing provided from the cassette 350, 370 to the handpiece 400. The surgeon typically makes an incision into the eye of the patient of a certain size and provides fluid into the eye while simultaneously removing unwanted lens material using ultrasonic power to break up the unwanted lens. The size of the incision is typically not known to the system, and traditionally has not been entered into the system. The present design seeks this information, in addition to other information (sleeve and tip size, etc.) and the system cannot sense the incision size. Size of the incision is therefore determined and provided to the system for purposes of determining the present conditions and a preferred course of action or warnings in such circumstances. Incision size may be provided as a single measurement or a measurement range and may be altered if desired.

Figure 4B:
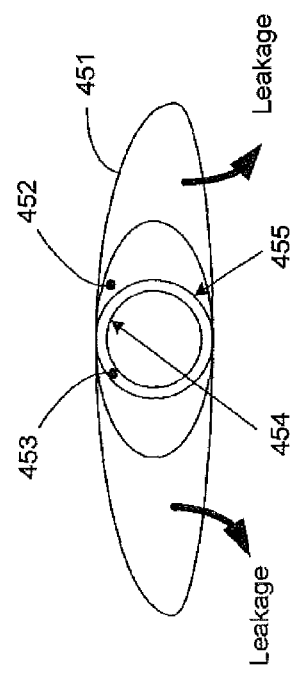
FIG. 4B shows an incision and components of the phaco handpiece employed within the incision.

FIG. 4B illustrates a drawing of an incision and the components employed during a surgical procedure. From FIG. 4B, incision 451 has been made, and the phaco handpiece, including the phaco sleeve 452 and phaco tip 453 provided through the incision 451. The phaco sleeve 452 has an outer diameter, while the phaco tip 453 has an inner diameter 454 and an outer diameter 455. In this situation, a considerable amount of the incision 451 is not taken up by the phaco handpiece components, with the result being a gap resulting in a certain amount of leakage. The present design employs the incision measurement, either a measurement or a range, together with the sleeve outer diameter, tip outer diameter, and tip inner diameter, to assess the flow conditions and the potential fluid issues and risks in order to determine warning conditions.

The handpiece typically provides fluid flow in the form of both irrigation and aspiration. In certain instances, the surgeon may employ one handpiece for irrigation/aspiration/ultrasonic energy or may employ more than one handpiece, such as one handpiece for providing fluid functionality (e.g. irrigation/aspiration (I/A) handpiece) and a second handpiece providing ultrasonic energy. In any situation, fluid flow to the eye must remain adequate based on the conditions encountered. Fluid flow in the present situation is generally a function of the outer diameter of the phaco tip and the inner diameter of the sleeve, as well as the incision size. In the case where the incision is excessively large, a sleeve having a small outer diameter may exhibit high rates of leakage, and such leakage can require additional aspiration pressure to maintain adequate flow from the eye as well as pressure in the eye.

Warning Design

Figure 5:
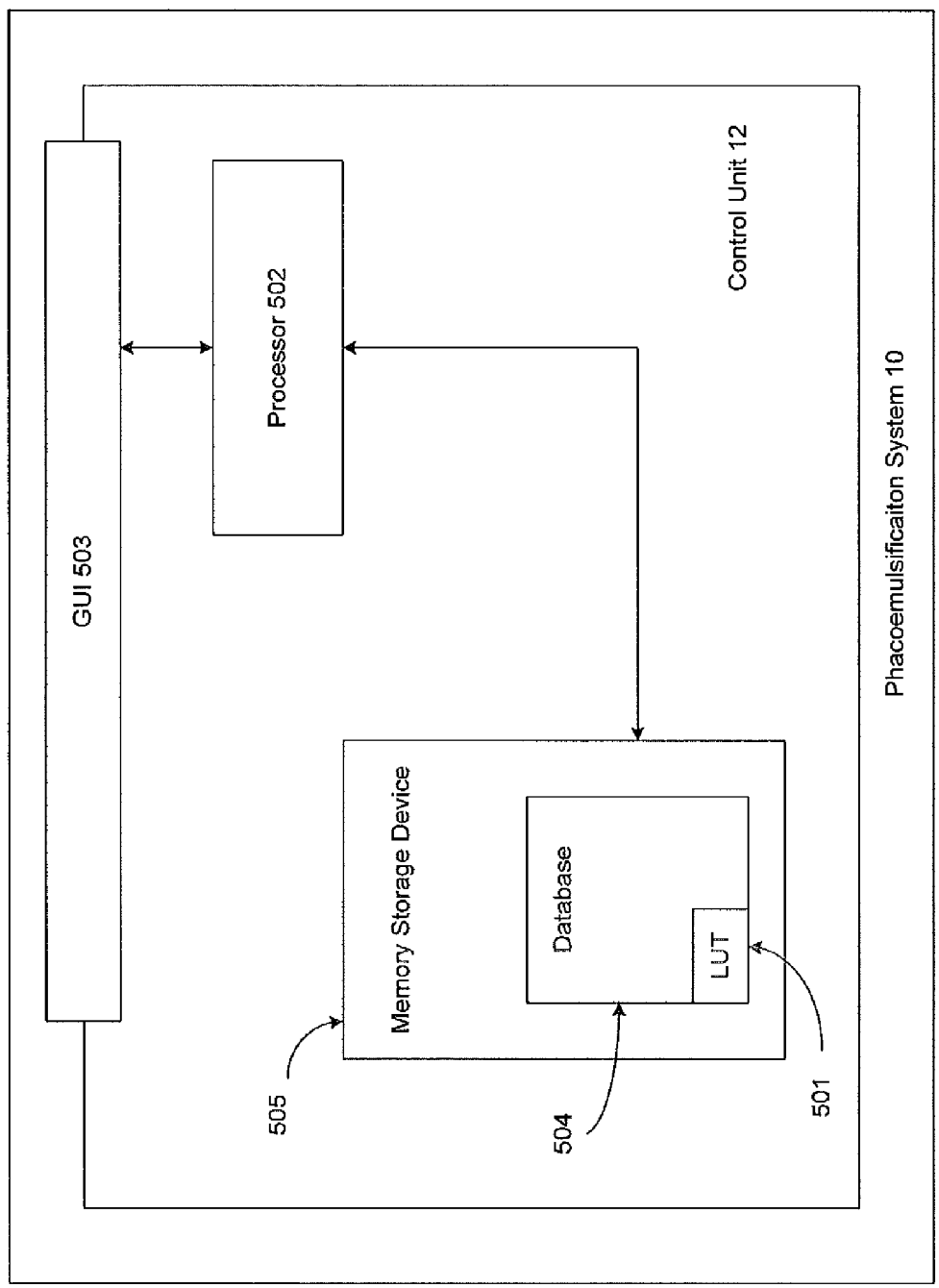
FIG. 5 is a simplified representation of components used to provide the warnings and functionality disclosed herein.

FIG. 5 is a general representation of certain components of the warning design provided herein. The present design considers pertinent fluidics conditions factors and provides certain warnings to an operator in cases where fluid flow to the eye may be inadequate, such as when the surgeon wishes to transition from one pump to another during a surgical procedure, such as from a peristaltic pump to a Venturi pump. The present design evaluates a series of fluid related parameters provided by operating room personnel, including expected pump usage and other pertinent fluid parameters. Such parameters may be entered pre-operation, i.e. before the surgical procedure, and the present design employs a processing device that consults with a lookup table that includes potential problem situations, i.e. situations where an inadequate or improper amount of fluid may potentially be provided to the patient's eye. In one scenario, a warning is provided to the operator that employing the desired parameters may result in an adverse condition. In another scenario, based on assessed risks, the system may inhibit functionality or alter functionality based on conditions encountered based on warning entries encountered.

The present design employs a lookup table 501 within a database 504 in a memory storage device 505 typically provided in the control unit 12 of phacoemulsification system 10. A processor 502 may be provided, and as noted, phacoemulsification system 10 may employ a graphical user interface 503 that enables operating room personnel to input relevant parameters and receive cautions or warnings. Warnings of varying degree may be provided, such as warnings that operating room personnel should, under no conditions, employ a particular fluid configuration, or warnings that are of little or no consequence, such as the proposed existence of conditions that are known to rarely or never cause any fluid flow issues. Based on the values and/or warning entries provided in the lookup table 501, the system may determine the conditions are unacceptable at some level and may provide a warning to the operator through the graphical user interface 503. For example, the phacoemulsification system 10 may display a warning indicating that use of certain requested components or settings may or will result in a hazardous or potentially hazardous condition.

Of particular interest is switching between pump types, i.e. from peristaltic to Venturi or vice versa. Peristaltic pumps typically employ some form of flow control, and vacuum builds only when an occlusion occurs. If the surgeon employs a "peristaltic" suite of tools and settings, such as a tip or sleeve typically used with peristaltic pumps and having a certain gauge, or opening, switching to Venturi with the "peristaltic" sleeve can enable excess fluid aspiration from the region, potentially causing a harmful condition.

Factors that may be considered, and potentially entered in the lookup table 501, include bottle height, incision size, number of incisions, sleeve type (with associated inner and outer diameters), phaco tip gauge (inner and outer diameters), port size (e.g. on an I/A handpiece, such as port sizes 0.3 or 0.5 IA), cut speed (for vitrectomy handpiece), pump or pumps employed, and maximum vacuum and/or maximum flow rate. Other fluid related parameters may also be employed. Certain of these parameters may not be known to the person interfacing with the phacoemulsification system 10 for this purpose, such as an operator not knowing the expected vacuum or flow rate to be used in a forthcoming ocular surgical procedure. In such circumstances, the device may provide warnings such as "do not switch between peristaltic and Venturi pumps using this configuration" or other warning.

The present device uses known circumstances triggering a potentially harmful condition based on the devices being employed and/or factors considered, and seeks to provide as much warning information as is appropriate under the circumstances. If no warning is required, i.e. if the warning level is below a threshold, no warning is provided to the operating room personnel entering the information. However, the present design seeks to consider as many factors as possible or known and provide warnings based on the information presented in view of known restrictions.

Numerous permutations exist with the number of factors considered, but one example is a situation where both peristaltic and Venturi pumps are to be employed during an ocular surgical procedure. The user may so indicate using the graphical user interface 503, and may also indicate a sleeve having an X gauge opening will be used, bottle height will always be less than B per cent of available height during the procedure, incision size is expected to be between P and Q millimeters, expected maximum flow is J, and expected maximum vacuum is K. Based on these conditions, which may be called input conditions, parameters, or simply conditions, processor 502 consults lookup table 501 in memory storage device 505. Lookup table 501 may indicate that the combination of X, B, P, Q, J, and K are acceptable when using both a peristaltic and Venturi pump. In such a case, the warning entry may simply indicate no warning is needed. As a result, no warning is given.

In the case where the combination of X, B, P, Q, J, and K are unacceptable when using both a peristaltic and Venturi pump, the warning entry in lookup table 501 may indicate that such operation may result in a harmful condition, and processor 502 may provide an indication of unacceptability to graphical user interface 503, such as "This configuration may result in a potentially harmful situation." Alternately, the system may notify the surgeon of the situation, may ask the surgeon or allow the surgeon to enable aspiration or bottle height adjustment(s) as he switches between pumps, and/or the system may automatically make adjustments as the surgeon switches between pumps. The automatic adjustments may be set forth in a look up table, preprogrammed by the surgeon, and/or are default settings on the system.

Particular functionality relating to known surgical components may be considered. For example, a database in the system may have information related to component X, such as a sleeve design, having an inside diameter of 0.4 mm, outside diameter of 0.6 mm, and so forth. Certain manufacturers also associate information with components, such as colors ("blue" sleeve, "yellow" sleeve, etc.) The database may maintain this information in the lookup table, and when presented with such information the system may employ the relevant parameters of such a component in making the determinations discussed herein. In certain circumstances, the components from multiple manufacturers may be supported, while in other circumstances components only from a single manufacturer may be supported. The lookup table will maintain all necessary information relating to the different components.

In one situation, components may be provided with some type of indication information, whether barcode, RFID, or other indication information known in the art. Such indication information must either be readable by a human or receivable by a computing device. Components may be scanned or otherwise determined by the system rather than manually entered by a surgeon or technician. Further, components may be grouped together and provided in a group using the aforementioned indication information, such as in a package bearing a barcode having a sleeve, needle, and any other desired materials (gloves, etc.).

While multiple components may be supported by a given system or a particular lookup table, a chance always exists that a component or set of components would be unknown to the system. In this failure condition, warnings may be provided as appropriate, anywhere from "It is recommended that you not perform surgery with this unknown component" to no warning at all depending on circumstances. In certain situations, personnel may be limited in components that may be employed during the surgical procedure, including potentially drastic actions such as not functioning in the presence of one unknown component. In this manner, components from unknown sources or unknown manufacturers may be limited or refused.

Figure 6:
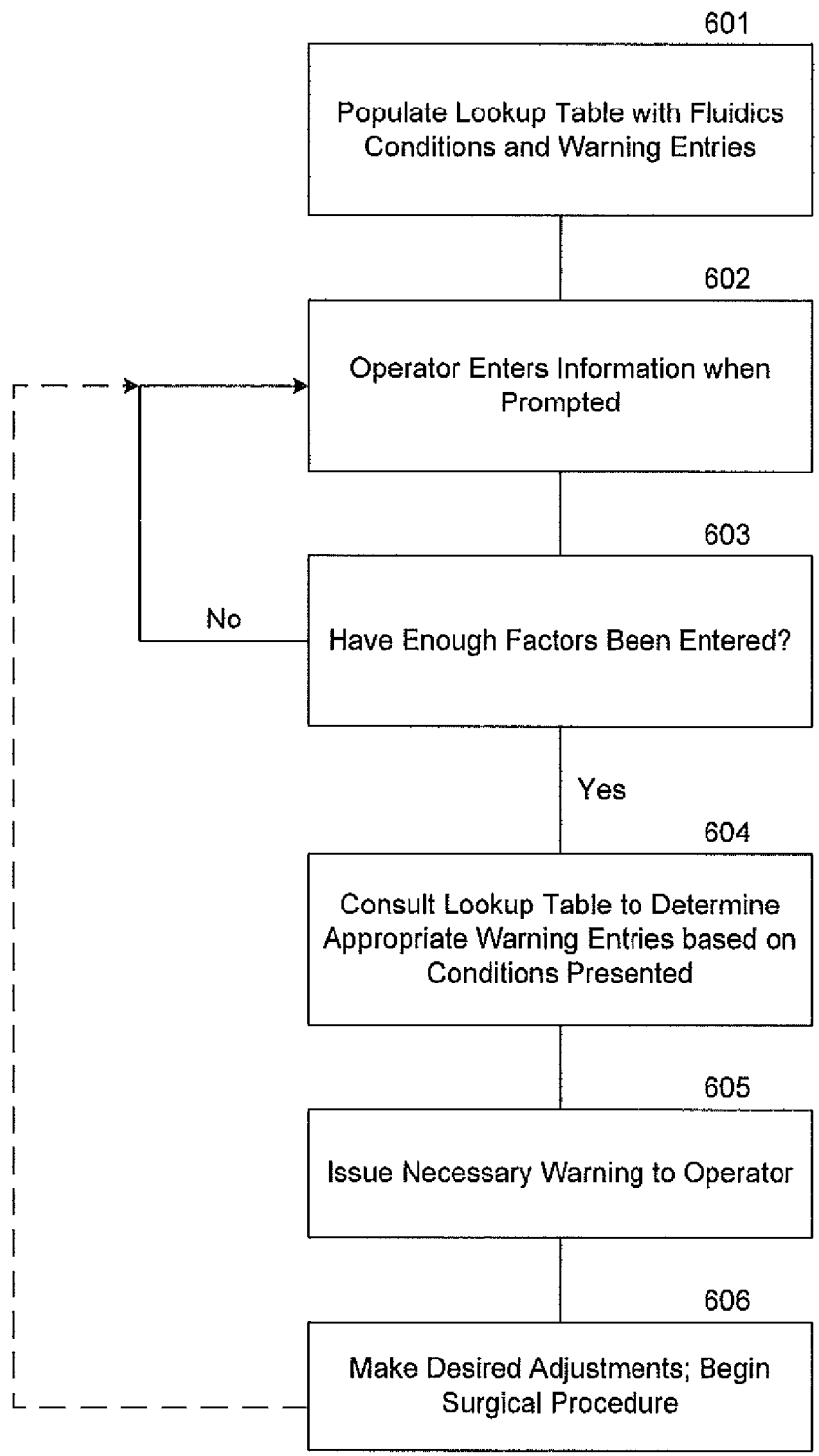
FIG. 6 is a flowchart of the operation of one aspect of the present design.

FIG. 6 illustrates a flowchart of one embodiment of the operation of the present design. Before deployment, element 601 indicates the lookup table 501 is populated with all possible fluidics permutations based on the factors potentially encountered. Permutations include both fluidics conditions that may be encountered, as well as warning entries, including situations where inadequate information is received, available, and/or provided. As an example, it may be known that 12 different types of handpiece sleeves may be used with handpiece H, each having a particular configuration (inside diameter, outside diameter, and so forth). Potential problematic conditions for all 12 types of sleeves may initially be provided to lookup table 501, and similarly, problematic conditions for other factors and/or components are also provided to the lookup table 501. The challenge for many practitioners is to understand and recall that a particular sleeve, or tip, or incision size, cannot be employed with a Venturi pump in the presence of certain conditions relating to bottle height, maximum fluid flow, and incision size. The present design evaluates all conditions and warns based on the conditions encountered.

Point 602 indicates the operator enters information when prompted. For example, the phacoemulsification system 10 may present the operator with at least one question such as "Will you be using a Venturi pump during the procedure?" or "What sleeve will you be using with handpiece H?" or "What is the maximum bottle height to be employed?" Such information may already be known or assumed by the phacoemulsification system 10 and may be stored in memory. Additionally, such information may be received from a storage device or component, such as a memory stick or loaded or transmitted from a handheld device (smartphone, tablet, etc.) or remote computing device to the phacoemulsification system 10. The operator may be given an option to override default values or values maintained in memory and may be given an opportunity to make change indications or requests to an existing or received profile.

For example, surgeon S may always operate using sleeve #SL6, needle #NE8, using both peristaltic and Venturi pumps, at a bottle height between setting #BH1 and #BH3, expected fluid flow rate of #FL44, maximum fluid flow rate of #FM60, with expected incision size during the contemplated procedure of #IN2. This information may be provided to the phacoemulsification system, either via manual entry or via transmission from a remote computing or storage device. Surgeon S or other personnel may indicate that Surgeon S will be making an incision in this instance of a different size, such as #IN4, and may require a fluid flow rate of #FM72, and thus may be offered the option to approve of existing settings or to change existing settings for Surgeon S. The operator may alternately or additionally be presented with a "confirmation" screen, asking her to confirm that certain relevant devices, settings, procedures, and/or parameters will be employed during the surgical procedure.

In the manual entry situation, the operator may also be queried as to the sleeve type or dimensions, tip type or dimensions, and/or incision size expected. The operator may enter all known conditions or cause such conditions to be provided to the system. At point 603, the phacoemulsification system 10 determines whether enough factors have been entered or made available. If not, the operator may be prompted for more information, such as via a message such as "A number of possible adverse conditions may be encountered using the limited number of settings provided. Please enter or provide more settings."

If enough settings have been entered or provided, the phacoemulsification system 10 may consult lookup table 501 at point 604 with the information and see which, if any, warnings are to be provided. In other words, once all information has been added or made available, the lookup table 501 and values provided or maintained in memory determine the relevant warning(s). As noted, certain information may be unavailable or unknown to the user. The lookup table 501 may be structured to take as many conditions available and generate an appropriate warning. For example, if only the type of handpiece, type of sleeve, pump(s) employed, and expected incision size are known, the lookup table 501 may use this information and generate a conditional warning, such as "if this condition occurs, operation at above this flow rate may result in a dangerous condition" and may make a recommendation, i.e. "It is recommended that you not use a Venturi pump with this configuration." Alternately, the recommendation provided may be "You are to reduce the vacuum setting from [X] when switching from peristaltic to Venturi pump," where X is a vacuum setting maintained in memory, or "The system will reduce the vacuum setting from [X] when switching from peristaltic to Venturi pump under these conditions." Other appropriate messages may be provided depending on circumstances.

Point 604 may be established in a type of logical "tree" or "branching" arrangement, where a first primary condition must be entered by the operator or provided to the phacoemulsification system 10, and when that condition is entered or received, the possible outcomes are provided, and the operator is prompted to enter a response or provide information responsive to a next level question, and so on, until enough information is obtained to provide a solution or the operator has indicated he does not know an expected parameter value or expected setting.

Point 605 issues an appropriate warning to the operator, or may issue no warning at all if all conditions are acceptable based on the lookup table 501. At point 606, depending on the conditions presented, the operator may change the type of instruments, components, or settings to be used, or may otherwise change the parameters or conditions expected to be used, and may again employ the design to assess the changed conditions, i.e. the operator may make changes and loop back through the flowchart of FIG. 6. Depending upon the type of warning, the system may also allow the operator to override the warning and proceed with the selected/chosen parameters.

Figure 7:
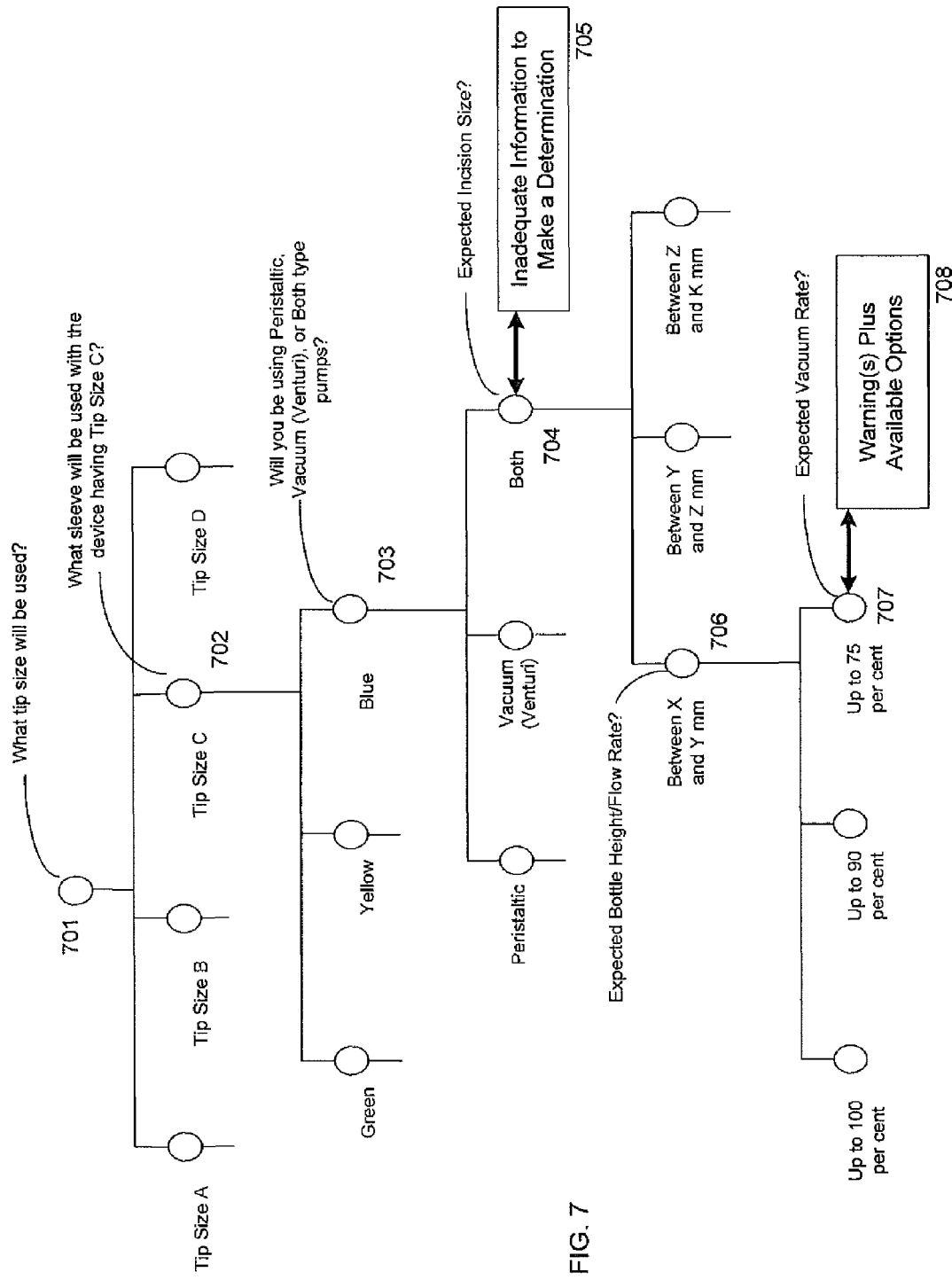
FIG. 7 illustrates an embodiment of an optional tree structure that may be used in the present design.

FIG. 7 illustrates a portion of a tree structure that may be employed in the branching of the present design. From FIG. 7, point 701 asks for the tip size being employed. Point 702 indicates Tip Size C is to be used, and the system subsequently asks the type of sleeve that will be employed with the device employing Tip Size C. The "blue" sleeve is indicated to be employed at point 703, and the system may then ask whether peristaltic, vacuum (Venturi), or both pumps will be employed. Alternately, the operator may select available memory settings that include all pump, bottle, and/or other relevant available operational settings, or provide information from a computing or storage device that certain devices or settings will be employed during the procedure. The operator may indicate at point 704 that both types of pumps are to be employed. The system then asks what size incision is expected to be available. The operator may be offered the option to indicate he does not know (not shown), at which point operation transitions to point 705, indicating that numerous adverse conditions may result, and again asks for an incision size. The user indicates between X and Y millimeters incision size, and the system then asks for expected bottle height at point 706. The user may indicate a bottle height of less than 75 per cent of maximum, and the system asks at point 707 about expected vacuum rate. The operator may not know this value, but at this point, enough information may be known to issue a warning, shown at point 708. After this, various options may be presented to the user, including starting over, entering a different condition or conditions if desired, such as using a different tip size, and proceeding with the tree/branching structure based on this different condition, or stopping operation. If the warning is that no adverse condition exists under any other fluidics condition, such an indication may also be provided.

The foregoing is intended as an example, and it is noted that branches not selected in the foregoing example are not shown in detail. In actual operation, numerous options may be presented in the tree or branching structure.

Figure 8:
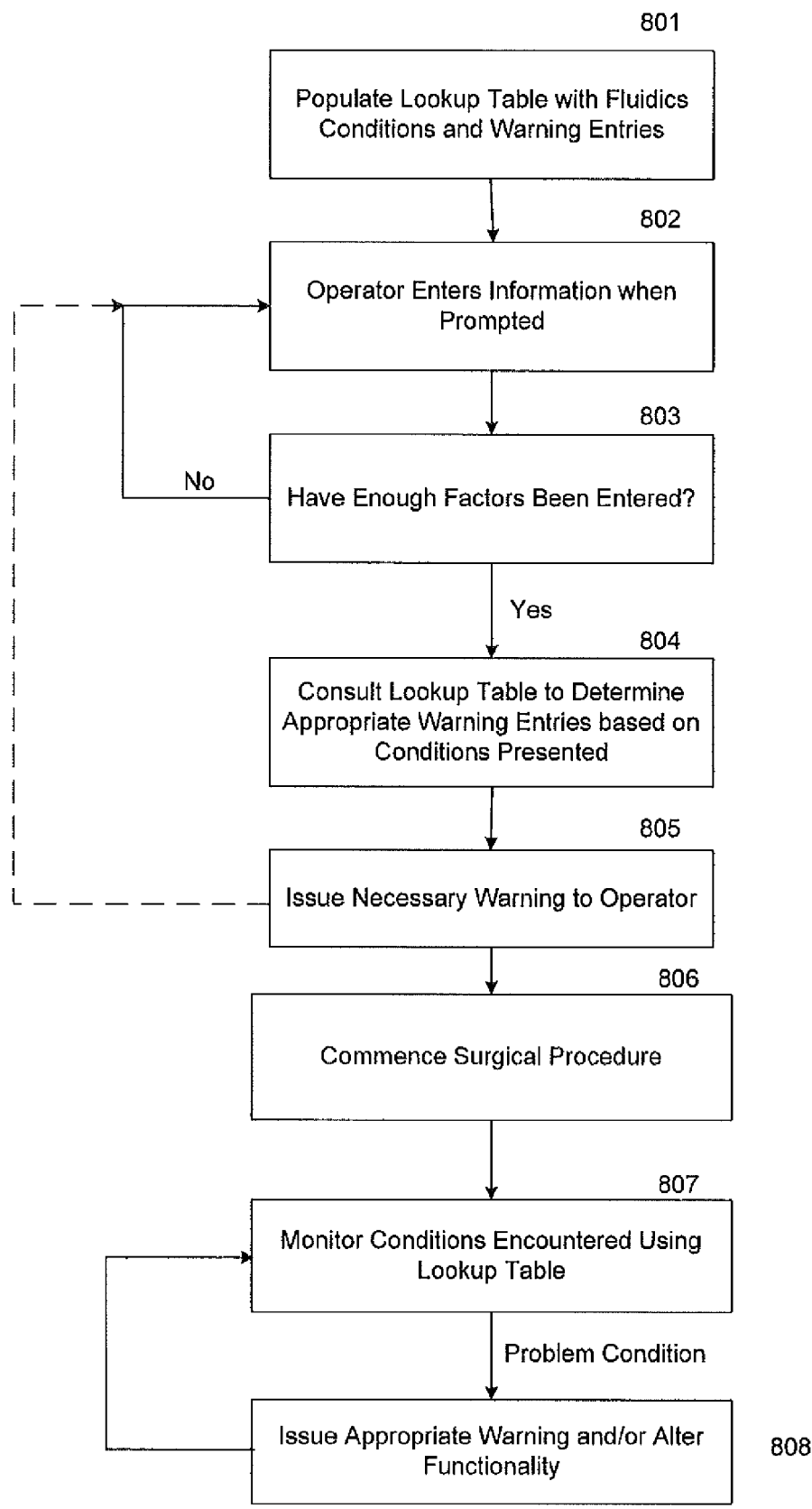
FIG. 8 shows a flowchart of an alternate design that may alter functionality if risks are deemed acceptable.

As surgery is a very exacting endeavor, warnings may be the best way to effectuate a successful outcome. If, however, risks are judged to be low enough, additional functionality may be provided. FIG. 8 illustrates an alternative embodiment that alters functionality rather than issuing warnings. From FIG. 8, element 801 indicates the lookup table is populated with all possible fluidics permutations based on the factors encountered as well as functional changes or commands to be executed in the event a specific fluidics condition exists. In certain instances, nothing will be done, while in other instances, functionality may be altered and/or warnings issued, while in the most extreme circumstances functionality may cease, e.g. the surgeon may be forbidden from switching from a peristaltic pump to a Venturi pump, the system may lower the vacuum setting to a "safe" level upon switching, and/or the maximum and/or minimum allowable value of settings may be adjusted to a "safe" level upon switching (e.g. vacuum, flow rate, ultrasonic energy). As previously discussed, different types of sleeves may be employed, as well as different handpieces, and so forth, and potential problematic conditions for all situations are provided to lookup table 501.

Point 802 indicates the operator may enter information when prompted, such as "What handpiece will be employed during the procedure?", "Will more than one type of handpiece be employed during the procedure?", "Will more than one type of pump be used?", "What is the maximum incision size expected to be encountered?", "How many incisions will be made?" and/or other appropriate questions. In certain limited instances, no questions may be asked, and the system may merely monitor conditions and alter functionality based on circumstances encountered. In other situations, answers to such questions may be provided from a remote computing device, or may be discerned by the system using information provided from a computing or storage device (smartphone, tablet, laptop, etc.) In one scenario, the operator enters all known or expected conditions.

At point 803, the phacoemulsification system 10 determines whether enough factors or conditions have been entered or are available. If not, the operator may be prompted for more information, such as via a message such as "A number of possible adverse conditions may be encountered using the limited number of settings provided. Please enter or provide more settings."

If enough settings have been entered or made available, the phacoemulsification system 10 may consult lookup table 501 at point 804 with the information and see which, if any, warnings are to be provided. The lookup table 501 may be structured to accept as many conditions are entered or available and may provide an appropriate warning. For example, if only the type of handpiece, type of sleeve, pump(s) employed, and expected incision size are known, the lookup table 501 may use this information and generate a conditional warning, such as "if X occurs, operation below a flow rate of Y may result in a dangerous condition" and may make a recommendation, i.e. "It is recommended that a smaller incision or a bottle height below 75% of maximum be employed during this procedure based on the conditions presented."

Again, point 804 may use a logical "tree" or "branching" arrangement, where a first primary condition must be entered or made available by the user, and when that condition is entered or made available, the possible outcomes are provided, and the operator is prompted to enter a response to a next level question, and so on, until enough information is obtained. It is understood that the lookup table provided may take the form of a table, with input entries corresponding to fluidics conditions expected to be encountered (flow rate, bottle height, incision size, number of incisions, etc.) and the values associated with these conditions forming warning entries, i.e. an entry warning against the particular condition encountered. Alternately, the lookup table may take the form of a branched tree, with certain nodes representing questions, and branches from those nodes representing possible responses to those questions. Other appropriate forms of a lookup table may be employed. While the term "lookup table" is employed herein, the term is intended broadly to encompass any arrangement wherein a set of inputs, values, or states are received and/or assessed and a set of warnings or actions are associated with the array, matrix, tree, or other arrangement representing an output or outputs with each group of conditions. Other entries or values or parameters may be provided as warnings, such as more information is needed, function X is to be performed, or nothing is required based on the conditions presented.

Point 805 issues any pre-surgery warnings and may again loop back if the operator wishes to change instruments, parameters, or other conditions. Point 806 indicates the procedure commences. Point 807 provides that the system monitors conditions encountered and the correlation between conditions encountered and the values (e.g. warning entries) provided in the lookup table. At point 808, if a condition is encountered based on expected performance and existing conditions, the system determines an action, where the action is specified based on the lookup table 501. The action may take the form of doing nothing, issuing a warning, or making a functional change, including actions such as changing bottle height, illustrated by the dotted line between IF 34 and computer 18 in FIG. 1, refusing to switch pumps and issuing a warning, shutting down some level of operation, requesting information be provided, providing a change over a period of time, such as altering vacuum from 50 per cent to 25 per cent over a 30 second period of time, or other appropriate action. Thus in the present embodiment, the lookup table 501 may include not only warnings, but also or alternatively commands to be executed by the phacoemulsification system 10 in the presence of certain conditions. Such functionality must account for risks associated with automated operation and may be prohibited if risks are judged to be excessive.

In one aspect of the present design, a warning may issue or functionality may be altered when phacoemulsification fluid performance corresponding to a level of performance outside a predetermined range is encountered. In these instances, any fluid parameter may be outside a predetermined range—high pressure, low pressure, high flow, low flow, inadequate fluid available, excessive fluid available, and so forth may result in a warning if so dictated by the lookup table. Values may be available to those skilled in the art and depend on various circumstances, i.e. excessive pressure in one situation may be different in another situation. Thus the predetermined value may depend on a variety of factors and circumstances, but as described herein, warnings may be provided or functionality altered when a fluid parameter may be or will be outside a desired or predetermined range.

While described herein in accordance with a phacoemulsification system, it is to be understood that the functionality described may be employed with any type of appropriate device, including but not limited to vitrectomy devices, devices employing two handpieces, known as a bimanual arrangement where two handpieces are employed, one providing fluid functionality and another providing, for example, ultrasonic functionality and optional fluid functionality, and other appropriate devices. With respect to vitrectomy devices, the cut speed of the vitrector would be a parameter or information entered into the system by an operator and part of the look up table for determining whether any conditions should be noted to the operator or parameters of the system changed. In general, any device having fluid flow sensitivity, including but not limited to devices having two types of pumps wherein operation during a procedure may switch from one pump to another, may employ the present design.

It is to be further understood that while fluid infusion is described herein primarily with respect to a bottle or fluid maintaining device, fluid may alternatively be provided by any type of fluid pressure source, and any control of infusion may occur by controlling either bottle height, as described, or pressure level or volume level of fluid provided by a fluid pressure source. Such a fluid pressure source may include any source of pressure that may be applied to a fluid wherein the result is fluid to a handpiece.

Thus according to one aspect of the present invention, there is provided a phacoemulsification device configured to receive fluid from a fluid maintaining device, the phacoemulsification device fluidly attached to a handpiece. The phacoemulsification device includes a control unit comprising a processor, a user interface configured to receive data from the processor and provide information to an operator, and a memory unit configured to provide information to the processor. The memory unit comprises a lookup table configured with a plurality of fluid parameter related conditions potentially expected to be encountered during a phacoemulsification procedure and a plurality of warning entries. Each warning entry is associated with fluid parameter related conditions potentially expected to be encountered during the phacoemulsification procedure. Each warning entry corresponding to a level of performance outside a predetermined range is conveyed to the operator via the user interface. In certain instances, each warning entry corresponding to a level of performance within the predetermined range is not conveyed to the operator.

The control unit may be further configured to provide relevant information obtained from the operator to the processor for assessment using the lookup table. The fluid parameter related conditions potentially expected to be encountered during the phacoemulsification procedure comprise at least one selected from the group consisting of height of the fluid maintaining device, incision size, number of incisions, sleeve type, type of pump employed, number of pumps employed, maximum vacuum, and maximum flow rate.

In one embodiment, during the phacoemulsification procedure, the control unit monitors a plurality of actual fluid parameter related conditions, and when the processor determines, based on the lookup table, that the actual fluid parameter related conditions are associated with one warning corresponding to a level of performance outside a predetermined range, the control unit alters fluid functionality of the phacoemulsification device. The lookup table may comprise a tree structure.

The handpiece may be configured with a sleeve having a fluid opening of a predetermined dimension, and the lookup table provides at least one warning entry based on the fluid opening of the sleeve. The phacoemulsification machine may also include a plurality of types of pumps (e.g. peristaltic and Venturi), and at least one warning entry warns against switching from one type pump to a second type pump.

Alternately, the present design may include a method of preparing for conducting a phacoemulsification procedure. The method may include querying a lookup table maintained on a control unit of a phacoemulsification device, the lookup table comprising a plurality of fluid parameter related conditions potentially expected to be encountered during the phacoemulsification procedure and a plurality of warning entries, each warning entry associated with fluid parameter related conditions potentially expected to be encountered during the phacoemulsification procedure, and issuing a warning to an operator when a warning entry for one fluid parameter related condition potentially expected to be encountered during the phacoemulsification procedure corresponds to a level of performance outside a predetermined range.

In another embodiment, the present design may include a phacoemulsification system comprising a control unit comprising a processor and a memory unit configured to provide information to the processor. The memory unit comprises a lookup table configured with a plurality of fluid parameter related conditions potentially expected to be encountered during a phacoemulsification procedure. Any set of fluid related conditions that according to the lookup table may potentially result in phacoemulsification system operating condition corresponding to a level of performance outside a predetermined range results in a change in fluid functionality of the phacoemulsification system.

Those of skill in the art will recognize that the step of a method described in connection with an embodiment may be interchanged without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A phacoemulsification system comprising:
   a control unit comprising:
      a processor;
      a memory unit configured to provide information to the processor, wherein the memory unit comprises a lookup table configured with a plurality of fluid parameter related conditions that may be encountered during a phacoemulsification procedure and a plurality of warning entries, each warning entry associated with at least one of the plurality of fluid parameter related conditions that may be encountered; and
      a user interface configured to receive data from the processor, provide information to an operator, and receive a plurality of input conditions from an operator for configuring the phacoemulsification system for a present phacoemulsification procedure; and
   wherein the processor is further configured to query the lookup table to determine if at least one warning entry needs to be issued to the operator based on the plurality of input conditions and the plurality of fluid parameter related conditions that may be encountered and to convey the at least one warning entry to the operator via the user interface prior to the start of the present phacoemulsification procedure when a warning entry for at least one of the plurality of fluid parameter related conditions expected to be encountered corresponds to a level of performance outside a predetermined range.

2. The phacoemulsification system of claim 1, wherein the control unit is further configured to provide information obtained to the processor for assessment using the lookup table.

3. The phacoemulsification system of claim 1, wherein the fluid parameter related conditions expected to be encountered procedure comprise at least one selected from the group consisting of height of a fluid maintaining device, incision size, number of incisions, sleeve type, type of pump employed, number of pumps employed, port size, expected cut rate, maximum vacuum, and maximum flow rate.

4. The phacoemulsification system of claim 1, wherein during the present phacoemulsification procedure, the control unit monitors a plurality of actual fluid parameter related conditions, and when the processor determines, based on the lookup table, that the actual fluid parameter related conditions are associated with one warning entry having severity above a predetermined level, the control unit alters fluid functionality of the phacoemulsification system.

5. The phacoemulsification system of claim 1, further comprising:
   a handpiece configured with a sleeve having a fluid opening of a predetermined dimension, wherein the lookup table provides at least one warning entry based on the fluid opening of the sleeve.

6. The phacoemulsification system of claim 1, wherein the lookup table comprises a tree structure.

7. The phacoemulsification system of claim 1, further comprising:
   a plurality of types of pumps, and at least one warning entry warns against switching from a first type pump to a second type pump.

8. The phacoemulsification system of claim 1, wherein each warning entry corresponding to a level of performance within the predetermined range is not conveyed to the operator.

9. The phacoemulsification system of claim 2, wherein the information obtained comprises desired settings obtained from one selected from the group consisting of a remote computing device and a remote storage device.

10. The phacoemulsification system of claim 1, wherein each warning entry is associated with at least two of the plurality of fluid parameter related conditions.

11. A method of alerting an operator to adverse conditions while preparing for conducting a phacoemulsification procedure, comprising:
  populating a lookup table maintained on a control unit of a phacoemulsification device with a plurality of fluid parameter related conditions that may be encountered during a phacoemulsification procedure and a plurality of warning entries, each warning entry associated with at least one of the plurality of fluid parameter related conditions that may be encountered;
  receiving, from an operator, a plurality of input conditions for configuring the phacoemulsification device for a present phacoemulsification procedure;
  querying the lookup table to determine if at least one warning needs to be issued to the operator based on the plurality of input conditions and the plurality of fluid parameter related conditions that may be encountered; and
  issuing the at least one warning to the operator prior to the start of the present phacoemulsification procedure when a warning entry for at least one of the plurality of fluid parameter related conditions expected to be encountered corresponds to a level of performance outside a predetermined range.

12. The method of claim 11, further comprising:
  before querying the lookup table, providing information to a processor in the phacoemulsification device for assessment using the lookup table.

13. The method of claim 11, wherein the plurality of fluid parameter related conditions expected to be encountered comprise at least one selected from the group consisting of height of a fluid maintaining device, incision size, number of incisions, sleeve type, type of pump employed, number of pumps employed, port size, cut rate, maximum vacuum, and maximum flow rate.

14. The method of claim 11, wherein the lookup table comprises a tree structure.

15. The method of claim 11, wherein at least one warning entry in the lookup table warns against switching from a first type pump to a second type pump.

16. The method of claim 11, wherein each warning entry corresponding to a level of performance within the predetermined range is not conveyed to the operator.

17. An apparatus comprising:
  a control unit comprising:
    a processor;
    a memory unit configured to provide information to the processor, wherein the memory unit comprises a lookup table configured with a plurality of fluid parameter related conditions that may be encountered during an ocular surgical procedure and a plurality of warning entries, each warning entry associated with at least one of the plurality of fluid parameter related conditions that may be encountered; and
    a user interface configured to provide data received from the processor to an operator and to receive a plurality of input conditions from the operator for configuring the apparatus for a present ocular surgical procedure; and
    wherein the processor is further configured to query the lookup table to determine if at least one warning entry needs to be issued to the operator based on the plurality of input conditions and the plurality of fluid parameter related conditions that may be encountered and to convey the at least one warning entry to the operator via the user interface prior to the start of the present phacoemulsification procedure when a warning entry corresponds to a level of performance outside a predetermined range.

18. The apparatus of claim 17, wherein the control unit is further configured to obtain information about the ocular surgical procedure and provide information obtained to the processor for assessment using the lookup table.

19. The apparatus of claim 17, wherein the plurality of fluid parameter related conditions expected to be encountered comprise at least one selected from the group consisting of height of a fluid maintaining device, incision size, number of incisions, sleeve type, type of pump employed, number of pumps employed, port size, cut rate, maximum vacuum, and maximum flow rate.

20. The apparatus of claim 17, wherein during the present ocular surgical procedure, the control unit monitors a plurality of actual fluid parameter related conditions, and when the processor determines, based on the lookup table, that the actual fluid parameter related conditions are associated with one warning entry having severity above a predetermined level, the control unit alters fluid functionality of the apparatus.

21. The apparatus of claim 17, wherein the lookup table comprises a tree structure.

22. The apparatus of claim 17, further comprising a plurality of types of pumps, and at least one warning entry warns against switching from a first type pump to a second type pump.

23. The apparatus of claim 17, wherein each warning entry corresponding to a level of performance within the predetermined range is not conveyed to the operator.

24. The apparatus of claim 18, wherein the information obtained comprises desired settings obtained from one selected from the group consisting of a remote computing device and a remote storage device.

25. The apparatus of claim 17, wherein each warning entry is associated with at least two of the plurality of fluid parameter related conditions expected to be encountered.

26. A phacoemulsification system comprising:
  a control unit comprising:
    a processor; and
    a memory unit configured to provide information to the processor; wherein the memory unit comprises a lookup table configured with a plurality of fluid parameter related conditions that may be encountered during a phacoemulsification procedure; and
    a user interface configured to receive data from the processor, provide information to an operator, and receive a plurality of input conditions from an operator for configuring the phacoemulsification system for a present phacoemulsification procedure; and
    wherein the processor is further configured to query the lookup table to determine if a change in fluid functionality of the phacoemulsification system is needed based on the plurality of input conditions and the plurality of fluid parameter related conditions that may be encountered and to change fluid functionality prior to the start of the present phacoemulsification procedure when a phacoemulsification system operating condition corresponding to a level of performance outside a predetermined range.

27. The phacoemulsification system of claim 26, further comprising additionally providing a warning when the phacoemulsification system operating condition corresponds to a level of performance outside the predetermined range.

28. The phacoemulsification system of claim 26, wherein the control unit is further configured to provide information obtained to the processor for assessment using the lookup table.

29. The phacoemulsification system of claim 26, wherein the plurality of fluid parameter related conditions that may be encountered during the phacoemulsification procedure comprise at least one selected from the group consisting of height of a fluid maintaining device, incision size, number of incisions, sleeve type, type of pump employed, number of pumps employed, port size, expected cut rate, maximum vacuum, and maximum flow rate.

30. The phacoemulsification system of claim 26, wherein during the phacoemulsification procedure, the control unit monitors a plurality of actual fluid parameter related conditions, and when the processor determines, based on the lookup table, that the actual fluid parameter related conditions are associated with one fluid condition having severity above a predetermined level, the control unit alters fluid functionality of the phacoemulsification system.

31. The phacoemulsification system of claim 26, further comprising:
a handpiece configured with a sleeve having a fluid opening of a predetermined dimension, wherein the lookup table provides at least one altered fluid function based on the fluid opening of the sleeve.

32. The phacoemulsification system of claim 26, wherein the lookup table comprises a tree structure.

33. The phacoemulsification system of claim 26, further comprising a plurality of types of pumps, wherein at least one fluid functionality change comprises altering switching from a first type pump to a second type pump.

34. The phacoemulsification system of claim 27, wherein each warning is audible to the operator.

35. The phacoemulsification system of claim 28, wherein the information obtained comprises desired settings obtained from one selected from the group consisting of a remote computing device and a remote storage device.

* * * * *